(12) United States Patent
Yoshiyama

(10) Patent No.: US 6,462,225 B2
(45) Date of Patent: Oct. 8, 2002

(54) METHOD FOR PRODUCING 2,2-DIMETHYL-3-(1-PROPENYL) CYCLOPROPANECARBOXYLATE ESTER

(75) Inventor: Tomonori Yoshiyama, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/741,868

(22) Filed: Dec. 22, 2000

(65) Prior Publication Data

US 2001/0014755 A1 Aug. 16, 2001

(30) Foreign Application Priority Data

Jan. 12, 2000 (JP) ........................................ 2000-003569

(51) Int. Cl.[7] .............................................. C07C 69/74
(52) U.S. Cl. ....................................... 560/124; 560/128
(58) Field of Search .................................. 560/124, 128

(56) References Cited

FOREIGN PATENT DOCUMENTS

GB              1446304      *    8/1976

OTHER PUBLICATIONS

Crombie et al, J. Chem. Soc. 1970 (c) pp. 1076–1080.*
Elliot et al, J. Chem. Perkin 1, 1974, pp. 2470–2474.*
L. Crombie, et al. "Synthesis of . . . and of Related Compounds", J. Chem. Soc., (C) 1970, pgs. 1076–1080.
M. Elliott, et al., "The Pyrethrins and Related . . . Substituents", J. Chem. Soc. Perkin I, 1974, pgs. 2470–2474.

* cited by examiner

Primary Examiner—Alan L. Rotman
Assistant Examiner—Hector M Reyes
(74) Attorney, Agent, or Firm—Fitch, Even, Tabin & Flannery

(57) ABSTRACT

An ester compound, which is a production intermediate of a pyrethroid compound, given by formula

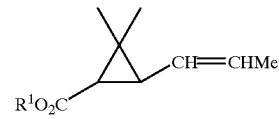

wherein $R^1$ represents $C_{1-6}$ alkyl group, etc., can be produced by allowing to react an aldehyde compound given by formula

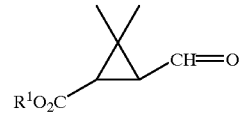

wherein $R^1$ has the same meaning above, with a phosphorane compound given by formula

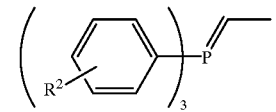

wherein $R^2$ represents a hydrogen atom, halogen atom or $C_{1-4}$ alkyl group, in an organic solvent, and obtaining a liquid distillate by heating the above reaction mixture with water in high yield.

8 Claims, No Drawings

METHOD FOR PRODUCING 2,2-DIMETHYL-3-(1-PROPENYL) CYCLOPROPANECARBOXYLATE ESTER

FIELD OF THE INVENTION

The present invention relates to a method for producing a 2,2-dimethyl-3-(1-propenyl)cyclopropanecarboxylate ester useful as an intermediate for preparing pyrethroid compounds which are active ingredients in insecticide or acaricides.

BACKGROUND ART

Prior, it has been known that certain ester compounds in which their acid part is 2,2-dimethyl-3-(1-propenyl) cyclopropanecarboxylic acid exhibit an excellent insecticidal effect in Japanese examined patent publication Nos. sho-54-3062B and sho-50-6629B. A method for producing 2,2-dimethyl-3-(1-propenyl)cyclopropanecarboxylate ester by Wittig reaction is known in J. Chem. Soc. (C), page 1076 (1970). The Wittig reaction is shown in the reaction formula below.

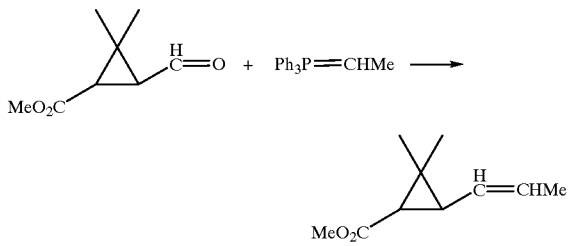

According to the description in the above-mentioned reference, work-up procedure needs an industrially disadvantageous several steps including filtration for isolating the objective 2,2-dimethyl-3-(1-propenyl) cyclopropanecarboxylate ester from the reaction mixture.

The present invention gives a beneficial method for producing 2,2-dimethyl-3-(1-propenyl) cyclopropanecarboxylate ester.

SUMMARY OF THE INVENTION

The present invention is a method for producing an ester compound given by formula (I):

wherein $R^1$ represents a $C_{1-6}$ alkyl group, $C_{3-6}$ cycloalkyl group, $C_{2-6}$ alkenyl group or $C_{4-6}$ cycloalkenyl group, which comprises allowing to react an aldehyde compound given by formula (II)

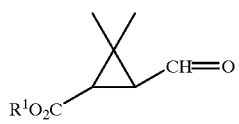

wherein $R^1$ has the same meaning above, with a phosphorane compound given by formula (III):

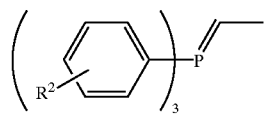

wherein $R^2$ represents a hydrogen atom, halogen atom or $C_{1-4}$ alkyl group, in an organic solvent, and obtaining a liquid distillate by heating the above reaction product with water.

The present method gives the ester compound given by formula (I) in high yield and by an industrially available procedure.

DETAILED DESCRIPTION

The present method is explained in detail below.

The present method generally contains two steps, namely a step for allowing to react an aldehyde compound given by formula (II) with a phosphorane compound given by formula (III) in an organic solvent to give a reaction product and another step for obtaining a liquid distillate by heating the reaction product obtained in the first step with water.

At first, the first step is explained below.

The first step is a reaction of an aldehyde compound given by formula (II) with a phosphorane compound given by formula (III) in an organic solvent and the phosphorane compound utilized in the first step can be prepared in the reaction system.

The organic solvent used in the first step is an inert solvent in Wittig reaction. Examples of such organic solvent include tetrahydrofuran, N,N-dimethylformamide, methyl t-butyl ether, ethylene glycol dimethyl ether, toluene, hexane, heptane and mixtures thereof.

The phosphorane compound can be prepared by a reaction of a phosphonium salt compound given by formula (IV):

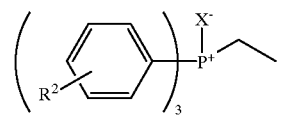

wherein X represents a chlorine atom or bromine atom and $R^2$ has the same meaning above, with a base. Examples of the utilized base include powdery sodium methoxide, potassium t-butoxide, potassium carbonate, sodium hydroxide and potassium hydroxide. The used amount of the base is usually 0.9 to 1.5 mols, preferably 1.0 to 1.3 mols, based on 1 mol of the phosphonium salt compound. The temperature for preparing the phosphorane compound is usually in the range of −20 to 120° C.

The phosphorane compound is used at a rate of 0.9 to 2.0 mols, preferably 1.0 to 1.2 mols, based on 1 mol of the aldehyde compound. In case that the phosphorane compound is prepared from the phosphonium salt compound, the phosphonium salt compound is used at a rate of 0.9 to 2.0 mols based on 1 mol of the aldehyde compound.

The reaction temperature of the first step is in the range of −20° C. to 120° C., preferably −10° C. and 30° C.

The reaction mixture obtained by the reaction of the aldehyde compound with the phosphorane compound can be provided to the second step as it is, though it may be subjected to neutralization by adding acidic water, such as diluted hydrochloric acid, diluted sulfuric acid and so on, to the reaction mixture for the sake of removing an excess of the base used in the preparation of the phosphorane compound.

Next, the second step is explained below.

The second step is a step for obtaining a liquid distillate containing the ester compound given by formula (I) by heating the reaction product obtained in the first step with water.

The amount of water utilized in the second step is usually one to 20 times parts by weight, preferably 5 to 10 times parts by weight based on one part by weight of the aldehyde compound used in the first step.

The method for heating the reaction product obtained in the first step with water is exemplified by a method for heating the total amount of the reaction product obtained in the first step with water in a vessel, a method for heating water in a vessel while adding gradually the reaction product obtained in the first step to the water, a method for heating the reaction product obtained in the first step in a vessel while adding water or blowing steam gradually to the reaction product and so on. These methods are usually carried out under atmospheric pressure and may be carried out under reduced pressure of 26.7 kPa (200 mmHg) or more.

The liquid distillate containing the ester compound given by formula (I) may also contain an organic solvent used in the first step and water. The water can be removed by phase separation and the separated water may be returned to the heating vessel. Concentration of the separated organic layer gives the ester compound given by formula (I) in high purity. The concentration can be performed by evaporation of the organic solvent under reduced pressure.

Further, by-products in the first step remain in the heating vessel of the second step. Though the by-products are precipitated, an adjustment of the amount of water in the vessel can make the precipitated slurry be undisturbed for stirring. The slurry gives phosphine oxide compound which can be recycled for preparing the corresponding phosphine compound, which is easily converted to the phosphonium salt compound given by formula (IV). The conversion of the phosphine oxide compound to the phosphine compound can be performed according to the method described in Chem. Lett., vol.10, pp.1491–1492 (1985).

As described above, the present invention makes it easy to separate the troublesome phosphine oxide compound off.

The aldehyde compound given by formula (II) can be prepared according to the production methods described in Japanese unexamined patent publication No. Hei2-225442A or Bull. Chem. Soc. Jpn., vol.60, pp.4385–4394 (1987). Further, the phosphonium salt compound given by formula (IV) can be prepared according to the description in Ann. Chem., vol.606, pp.1–23 (1957).

Examples of the alkyl group represented by $R^1$ include methyl group, ethyl group, propyl group, isopropyl group, butyl group, isobutyl group, t-butyl group, pentyl group, hexyl group, 2-methylpentyl group and 2,3-dimethylbutyl group, and examples of the cycloalkyl group represented by $R^1$ include cyclopropyl group, cyclopentyl group and cyclohexyl group. Example of the alkenyl group represented by $R^1$ include 2-propenyl group, 3-butenyl group and 2-butenyl group, and examples of cycloalkenyl group represented by $R^1$ include cyclopentenyl group and cyclohexenyl group.

Examples of the alkyl group represented by $R^2$ include methyl group substituted at 3-position of phenyl group and chlorine atom substituted at 4-position of phenyl group.

EXAMPLES

Hereinafter, the present invention is explained in more detail below referring to an example but the present invention should not be limited in the following example.

Production Example 1

In a 500-mililiter four-neck round-bottom flask assembled with a shaft with blade, a suspension of 20.3 g of sodium methoxide in 138.8 g of tetrahydrofuran was cooled to 0° C. and thereto 111.5 g of triphenylethylphosphonium bromide was added over 5 minutes under a nitrogen atmosphere. After stirring for one hour at 0 to 5° C., 73.3 g of toluene solution of methyl trans-2,2-dimethyl-3-formylcyclopropanecarboxylate (containing 39.1 g of pure methyl trans-2,2-dimethyl-3-formylcyclopropanecarboxylate) was added dropwise to the reaction mixture over 5.5 hours at the same temperature. Then, after stirring for 1.5 hours at the same temperature, 42.0 g of 10% (by weight) hydrochloric acid was added dropwise to the reaction mixture to adjust pH of the water layer to 6.85. To the reaction mixture, 198.9 g of water was added and heated to concentrate until 130 ml of a mixture of toluene and tetrahydrofuran was evaporated at 74 to 82° C. Then, 192.8 g of water was added to the residue and distilled at 84.6 to 102.1° C. (109 to 131° C. at bath temperature), while 391 g of water was added over 4.5 hours after the inner temperature reached 93° C. The distillate was separated to 411.7 g of water and 73.4 g of organic layer. The obtained organic layer contains 53.7% (by weight) of methyl 2,2-dimethyl-3-(1-propenyl) cyclopropanecarboxylate (analyzed by internal standard method of gas chromatography; The analytical condition of gas chromatography is described below.).

Further, 72.3 g of the obtained organic layer was subjected to concentration under reduced pressure to give 38.7 g of methyl 2,2-dimethyl-3-(1-propenyl) cyclopropanecarboxylate (yield: 91.9%). The isolated methyl 2,2-dimethyl-3-(1-propenyl) cyclopropanecarboxylate is a mixture of two isomers below:

Methyl trans-2,2-dimethyl-3-((E)-1-propenyl) cyclopropanecarboxylate

Methyl trans-2,2-dimethyl-3-((Z)-1-propenyl) cyclopropanecarboxylate=9.5:90.5 wherein E and Z represent geometrical isomerism based on 1-propenyl group.

The E/Z ratio is estimated by gas chromatography analysis.

1H-NMR (CDCl$_3$, TMS as internal standard) δ (ppm) 1.14 (s,3H), 1.27(s,3H), 1.45(d,1H), 2.75(dd,1H), 3.68(s,3H), 5.05–5.18(m,1H), 5.52-5.68(m, 1H).

Analytical Condition of Gas Chromatography

Column: Capillary column DB-1 (manufactured by J&W SCIENTIFIC) length 30m, diameter 0.53 mm, membrane thickness 1.5 g m Column temperature: from 70° C., raising temperature at 2° C./minute to 100° C., keeping 10 minutes at the same temperature and raising temperature at 10° C./minute to 300° C.

Detector: FID

Injection temperature: 270° C.

Detector temperature: 310° C.

Carrier gas: helium (flow rate: 5 ml/minute)

What is claimed is:

1. A method for producing an ester compound represented by formula

wherein $R^1$ represents a $C_{1-6}$ alkyl group, $C_{3-6}$ cycloalkyl group, $C_{2-6}$ alkenyl group or $C_{4-6}$ cycloalkenyl group which comprises allowing an aldehyde compound represented by formula

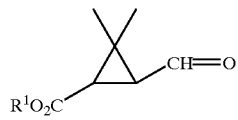

wherein $R^1$ has the same meaning above, to react with a phosphorane compound represented by formula

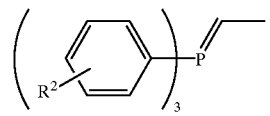

wherein $R^2$ represents a hydrogen atom, halogen atom or $C_{1-4}$ alkyl group, in an organic solvent, and obtaining a liquid distillate by (a) adding water to the reaction mixture and heating, (b) heating water while adding the reaction mixture to the water, or (c) heating the reaction mixture while adding water or blowing steam to the reaction mixture.

2. The method according to claim 1, wherein $R^1$ is a methyl group, ethyl group, propyl group or isopropyl group.

3. The method according to claim 1, wherein the organic solvent is tetrahydrofuran, N,N-dimethylformamide, methyl t-butyl ether, ethylene glycol dimethyl ether, toluene, hexane, heptane or mixture thereof.

4. The method according to claim 1, wherein the organic solvent is tetrahydrofuran, toluene or mixture thereof.

5. A method of producing an ester compound represented by formula

wherein $R^1$ represents a $C_{1-6}$ alkyl group, $C_{3-6}$ cycloalkyl group, $C_{2-6}$ alkenyl group or $C_{4-6}$ cycloalkenyl group, which comprises allowing to react an aldehyde compound represented by formula

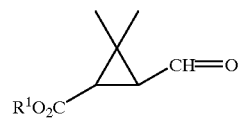

wherein $R^1$ has the same meaning above, with a phosphorane compound represented by formula

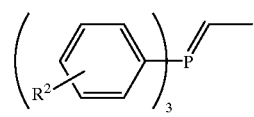

wherein $R^2$ represents a hydrogen atom, halogen atom or $C_{1-4}$ alkyl group, in an organic solvent, obtaining a liquid distillate by heating the above reaction mixture with water, removing water by phase separation and evaporating the organic solvent.

6. The method according to claim 5, wherein $R^1$ is a methyl group, ethyl group, propyl group or isopropyl group.

7. The method according to claim 5, wherein the organic solvent is tetrahydrofuran, N,N-dimethylformamide, methyl t-butyl ether, ethylene glycol dimethyl ether, toluene, hexane, heptane or mixture thereof.

8. The method according to claim 5, wherein the organic solvent is tetrahydrofuran, toluene or mixture thereof.

* * * * *